US009480727B2

(12) United States Patent
Kobayashi et al.

(10) Patent No.: US 9,480,727 B2
(45) Date of Patent: Nov. 1, 2016

(54) SYNTHETIC PEPTIDE FOR INHIBITING EXPRESSION OF TYPE 2 TNF RECEPTOR AND USE THEREOF

(71) Applicant: TOAGOSEI CO., LTD., Tokyo (JP)

(72) Inventors: Nahoko Kobayashi, Tsukuba (JP); Tetsuhiko Yoshida, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

(21) Appl. No.: 14/432,326

(22) PCT Filed: Oct. 17, 2013

(86) PCT No.: PCT/JP2013/078222
§ 371 (c)(1),
(2) Date: Mar. 30, 2015

(87) PCT Pub. No.: WO2014/061749
PCT Pub. Date: Apr. 24, 2014

(65) Prior Publication Data
US 2015/0273018 A1   Oct. 1, 2015

(30) Foreign Application Priority Data

Oct. 18, 2012   (JP) .................................. 2012-231148

(51) Int. Cl.
*A61K 38/17*   (2006.01)
(52) U.S. Cl.
CPC .................................. *A61K 38/1716* (2013.01)
(58) Field of Classification Search
None
See application file for complete search history.

(56) References Cited

U.S. PATENT DOCUMENTS

| | | | |
|---|---|---|---|
| 4,578,269 A | 3/1986 | Morein | |
| 4,744,983 A | 5/1988 | Morein | |
| 4,867,975 A | 9/1989 | Gelb, Jr. | |
| 4,981,684 A | 1/1991 | MacKenzie et al. | |
| 5,178,860 A | 1/1993 | MacKenzie et al. | |
| 5,242,932 A | 9/1993 | Gandy et al. | |
| 5,441,931 A | 8/1995 | Sprecher et al. | |
| 5,519,003 A | 5/1996 | Mochly-Rosen et al. | |
| 5,679,355 A | 10/1997 | Alexander et al. | |
| 5,961,970 A | 10/1999 | Lowell et al. | |
| 6,037,521 A | 3/2000 | Sato et al. | |
| 6,333,167 B1 | 12/2001 | Quinet et al. | |
| 6,340,583 B1 | 1/2002 | Yan et al. | |
| 6,403,353 B1 | 6/2002 | Yan et al. | |
| 6,423,684 B1 | 7/2002 | Mochly-Rosen et al. | |
| 6,476,189 B1 | 11/2002 | Yamakawa et al. | |
| 8,822,408 B2 * | 9/2014 | Yoshida ............. | C07K 14/4711 435/377 |
| 2003/0125242 A1 | 7/2003 | Rosenecker et al. | |
| 2003/0166215 A1 | 9/2003 | Yan et al. | |
| 2003/0229202 A1 | 12/2003 | Guo et al. | |
| 2004/0175751 A1 | 9/2004 | Yan et al. | |
| 2004/0186052 A1 | 9/2004 | Iyer et al. | |
| 2004/0226056 A1 | 11/2004 | Roch et al. | |
| 2005/0129701 A1 | 6/2005 | Marasco et al. | |
| 2006/0057668 A1 | 3/2006 | Yoshida et al. | |
| 2006/0100134 A1 | 5/2006 | Guo et al. | |
| 2006/0166917 A1 | 7/2006 | Lindeman et al. | |
| 2006/0270834 A1 | 11/2006 | Kanno | |
| 2007/0065941 A1 | 3/2007 | Kondo et al. | |
| 2008/0076145 A1 | 3/2008 | Cummings et al. | |
| 2009/0004144 A1 | 1/2009 | Tabira et al. | |
| 2009/0253618 A1 | 10/2009 | Kanno et al. | |
| 2010/0074925 A1 | 3/2010 | Carmon | |
| 2010/0093059 A1 | 4/2010 | Wolff et al. | |
| 2010/0169988 A1 | 7/2010 | Kohli et al. | |
| 2010/0209490 A1 | 8/2010 | Morita et al. | |
| 2010/0297758 A1 | 11/2010 | Yoshida et al. | |
| 2011/0229912 A1 | 9/2011 | Cai et al. | |
| 2011/0269942 A1 | 11/2011 | Morita et al. | |
| 2012/0035112 A1 * | 2/2012 | Yoshida ............. | C07K 14/4756 514/17.7 |
| 2012/0122210 A1 | 5/2012 | Yoshida et al. | |
| 2012/0122225 A1 | 5/2012 | Kobayashi et al. | |
| 2012/0208752 A1 | 8/2012 | Yoshida et al. | |
| 2013/0005034 A1 | 1/2013 | Yoshida et al. | |
| 2013/0079273 A1 | 3/2013 | Yoshida et al. | |
| 2013/0345408 A1 | 12/2013 | Fukushima et al. | |

(Continued)

FOREIGN PATENT DOCUMENTS

| | | |
|---|---|---|
| EP | 0 653 154 A2 | 5/1995 |
| EP | 1 634 956 A1 | 3/2006 |

(Continued)

OTHER PUBLICATIONS

Beck et al. Amyloid precursor protein in guinea pigs—complete cDNA sequence and alternative splicing. Biochim Biophys Acta. Mar. 20, 1997;1351(1-2):17-21.*

(Continued)

*Primary Examiner* — David Romeo
(74) *Attorney, Agent, or Firm* — Oliff PLC (57) ABSTRACT

This invention provides an artificially synthesized peptide having an activity to inhibit the expression of type 2 TNF receptor (TNF-R2), and a TNF-R2 expression-inhibiting composition including the peptide as an active ingredient. Also provided is a method for inhibiting the expression of TNF-R2 in cells capable of expressing TNF-R2, by using the peptide. The expression of TNF-R2 in the cells is inhibited, by supplying the cells capable of expressing TNF-R2 with a synthetic peptide essentially including of an amino acid sequence constituting a signal peptide in an amyloid precursor protein (APP) or an amino acid sequence formed by substituting, deleting and/or adding one or several amino acid residues in/from/to the amino acid sequence of the signal peptide.

6 Claims, 1 Drawing Sheet

(56) References Cited

U.S. PATENT DOCUMENTS

| | | | |
|---|---|---|---|
| 2014/0072592 | A1 | 3/2014 | Okamoto et al. |
| 2014/0178990 | A1 | 6/2014 | Yoshida et al. |
| 2014/0335613 | A1 | 11/2014 | Yoshida et al. |
| 2015/0126434 | A1 | 5/2015 | Kobayashi et al. |

FOREIGN PATENT DOCUMENTS

| | | | |
|---|---|---|---|
| EP | 1 918 297 A1 | 5/2008 | |
| JP | 69-186921 A | 10/1984 | |
| JP | 07-132033 A | 5/1995 | |
| JP | 07-505389 A | 6/1995 | |
| JP | 09-323928 A | 12/1997 | |
| JP | 2000063400 A | 2/2000 | |
| JP | 2001-199997 A | 7/2001 | |
| JP | 2001186887 A | 7/2001 | |
| JP | 2003-137899 A | 5/2003 | |
| JP | 2004-357543 A | 12/2004 | |
| JP | 2005-511047 A | 4/2005 | |
| JP | 2005-154338 A | 6/2005 | |
| JP | 2005-330206 A | 12/2005 | |
| JP | 3854995 B2 | 12/2006 | |
| JP | 2007-145761 A | 6/2007 | |
| JP | 2007-159429 A | 6/2007 | |
| JP | 2007-517057 A | 6/2007 | |
| JP | 2009-209064 A | 9/2009 | |
| JP | 2011-016763 A | 1/2011 | |
| JP | 2012-518042 A | 8/2012 | |
| WO | 95/21252 A2 | 8/1995 | |
| WO | 02/18572 A2 | 3/2002 | |
| WO | 02/077171 A2 | 10/2002 | |
| WO | 03/048337 A2 | 6/2003 | |
| WO | 03/076561 A2 | 9/2003 | |
| WO | 0391429 A1 | 11/2003 | |
| WO | 2004/056854 A1 | 7/2004 | |
| WO | 2005/086800 A2 | 9/2005 | |
| WO | 2007/010989 A1 | 1/2007 | |
| WO | 2007/149293 A2 | 12/2007 | |
| WO | 2008/008569 A2 | 1/2008 | |
| WO | 2008/027017 A1 | 3/2008 | |
| WO | 2008/035350 A1 | 3/2008 | |
| WO | 2008/125360 A1 | 10/2008 | |
| WO | 2009/020093 A1 | 2/2009 | |
| WO | 2009/020094 A1 | 2/2009 | |
| WO | 2009/047002 A2 | 4/2009 | |
| WO | 2009/053696 A1 | 4/2009 | |
| WO | 2009/093692 A1 | 7/2009 | |
| WO | 2010/096470 A2 | 8/2010 | |
| WO | 2010/117078 A1 | 10/2010 | |
| WO | 2010117079 A1 | 10/2010 | |
| WO | 2011/052679 A1 | 5/2011 | |
| WO | 2011/152524 A1 | 12/2011 | |
| WO | WO 2011/152524 A | * 12/2011 | |
| WO | 2012093706 A1 | 7/2012 | |
| WO | 2012093732 A1 | 7/2012 | |

OTHER PUBLICATIONS

Böcker et al. IKK-2 is required for TNF-alpha-induced invasion and proliferation of human mesenchymal stem cells. J Mol Med (Berl). Oct. 2008;86(10):1183-92.*

Oerum et al. Porcine APP cDNAs: molecular cloning and characterization, expression analysis, chromosomal localization and SNP analysis. Biochim Biophys Acta. Jul. 2006;1759(7):378-84. Epub Jul. 14, 2006.*

Retinal Diseases, in MeSH Database, National Center for Biotechnology Information, Bethesda, Maryland, USA [online], [retrieved on Dec. 27, 2015]. Retrieved from the Internet: <URL: http://www.ncbi.nlm.nih.gov/mesh/?term=retinal+diseases&report=Full&format=text>.*

McKinnon et al., "Neuroinflammation in Glaucoma," XIX Biennial Meeting of The International Society for Eye Research, Jul. 18-23, 2010, Montreal, Canada.

Luo et al., "Differential Functions of Tumor Necrosis Factor Receptor 1 and 2 Signaling in Ischemia-Mediated Arteriogenesis and Angiogenesis," The American Journal of Pathology, pp. 1886-1898, vol. 169, No. 5, Nov. 2006.

Nakazawa et al., "Tumor Necrosis Factor-α Mediates Photoreceptor Death in a Rodent Model of Retinal Detachment," Investigative Opthamology & Visual Science, pp. 1384-1391, vol. 52, No. 3, Mar. 2011.

Clark et al., "Is TNF a Link between Aging-Related Reproductive Endocrine Dyscrasia and Alzheimer's Disease?" Journal of Alzheimer's Disease, pp. 691-699, vol. 27, 2011.

Nov. 12, 2013 International Search Report issued in International Application No. PCT/JP2013/078222.

Apr. 21, 2015 International Preliminary Report on Patentability issued in International Application No. PCT/JP2013/078222.

Sim et al., "Ligand-Dependent Activation of the Chimeric Tumor Necrosis Factor Receptor-Amyloid Precursor Protein (APP) Reveals Increased APP Processing and Suppressed Neuronal Differentiation," Neurosignals, pp. 9-23, vol. 18, 2010.

Dec. 18, 2014 Notification of Reasons for Refusal issued in Japanese Application No. 2011-538478.

Cells-Merck Manual, from http://www.merckmanuals.com/home/fundamentals/ the_human_body/cells.html, pp. 1-2, accessed Dec. 24, 2014.

DNA and cell division, from http://www.bbc.co.uk/schools/gcsebitesize/science/ add_aqa/inheritance/dna_cell_division . . . , pages 1-6, accessed Dec. 28, 2014.

O'Sullivan et al., "Cytokine Receptor Signaling Through the Jak-Stat-Socs Pathway in Disease," Molecular Immunology, vol. 44, pp. 2497-2506, 2007.

Stem cell information, from http://stemcells.nih.gov/StaticResources/info/ popups/glossary.html, pp. 1-6, accessed Dec. 23, 2014.

Woodbury et al., "Adult Rat and Human Bone Marrow Stromal Cells Differentiate Into Neurons," Journal of Neuroscience Research, vol. 61, pp. 364-370, 2000.

Jan. 23, 2015 Office Action issued in U.S. Appl. No. 14/163,371.

Jun. 25, 2013 Search Report issued in International Application No. PCT/JP2013/064393.

Soscia, Stephanie et al. "The Alzheimer's Disease-Associated Amyloid b-Protein Is an Antimicrobial Peptide". vol. 5, 1-10, 2010. PLoS One.

Martoglio, Bruno et al. "Signal sequences: more than just greasy peptides". vol. 8, 410-415, 1998, trends in Cell Biology.

Papareddy, Praveen et al. "Antimicrobial activity of peptides derived from human b-amyloid precursor protein". vol. 18, 183-191, 2012, Journal of Peptide Science.

Panegyres, Peter et al. "The Functions of the Amyloid Precursor Protein Gene and Its Derivative Peptides: I Molecular Biology and Metabolic Processing". vol. 2, 120-131, 2011, Neuroscience & Medicine.

Strooper, Bart et al. "Proteolytic processing and cell biological functions of the amyloid precursor protein". vol. 113, 1857-1870, 2000, Journal of Cell Science.

Dec. 2, 2014 International Preliminary Report on Patentability issued in International Application No. PCT/JP2013/064393.

Paliga et al., "Human Amyloid Precursor-like Protein 1 cDNA Cloning, Ectopic Expression in COS-7 Cells and Identification of Soluble Forms in the Cerebrospinal Fluid," Eur. J. Biochem., vol. 250, pp. 354-363, 1997.

Lichtenthaler et al., "A Novel Substrate for Analyzing Alzheimer's Disease g-Secretase," FEBS Letters, vol. 453, pp. 288-292, 1999.

Rohn et al., "A Monoclonal Antibody to Amyloid Precursor Protein Induces Neuronal Apoptosis," Journal of Neurochemistry, vol. 74, pp. 2331-2342, 2000.

Kohler et al., "Continuous Cultures of Fused Cells Secreting Antibody of Predefined Specificity," Nature, vol. 256, pp. 195-497, Aug. 7, 1975.

Henderson et al., "HLA-A2.1-Associated Peptides from a Mutant Cell Line: A Second Pathway of Antigen Presentation," Science, 1992, vol. 255, pp. 1264-1266.

(56) References Cited

OTHER PUBLICATIONS

Hage et al., "Preprocalcitonin Signal Peptide Generates a Cytotoxic T Lymphocyte-Defined Tumor Epitope Processed by a Proteasome-Independent Pathway," PNAS, Jul. 2008, vol. 105, No. 29, pp. 10119-10124.
Abbott, "The Plaque Plan," Nature, Nov. 2008, vol. 456, pp. 161-164.
Nikolaev et al., "APP Binds DR6 to Trigger Axon Pruning and Neuron Death via Distinct Caspases," Nature, Feb. 2009, vol. 457, pp. 981-989.
Mar. 13, 2012 International Search Report issued in International Patent Application No. PCT/JP2012/050210.
Jul. 10, 2013 International Preliminary Report on Patentability issued in International Patent Application No. PCT/JP2012/050210.
Harlow et al., Antibodies; A Laboratory Manual, Spring Harbor Laboratory, 1988, Chapter 5, pp. 72-77.
Hopp et al., "Prediction of Protein Antigenic Determinants from Amino Acid Sequences," Proc. Natl. Acad. Sci. USA, 1981, vol. 78, No. 6, pp. 3824-3828.
Water, from http://www.biology-online.org/dictionary/Water, pp. 1-3, accessed Apr. 24, 2014.
DSMO—The Source Natural Foods, from http://thesourcenatural.com/ . . . isplayMonograph.asp?storeID=dhap6v4fb7sr2nm700akhlbd3cmfbxmd&DocID=bottomline-dimethylsulfoxide, pp. 1-7, accessed Sep. 23, 2015.
Hilton et al., "Anti-Peptide Antibody Blocks Peptide Binding to MHC Class I Molecules in the Endoplasmic Reticulum", Journal of Immunology, vol. 166, pp. 3952-3956, 2001.
Pomroy et al., "Solubilization of Hydrophobic Peptides by Reversible Cysteine PEGylation", Biochemical and Biophysical Research Communications, vol. 245, No. 2, pp. 618-621, 1998.
Boulant et al., "Hepatitis C Virus Core Protein is a Dimeric Alpha-Helical Protein Exhibiting Membrane Protein Features", Journal of Virology, vol. 79, No. 17, pp. 11353-11365,2005.
Extended European Search Report for European Patent Application No. 12731948.1, mailed Jul. 14, 2015.
Kobayashi et al., 1. Biosci. Bioeng., vol. 86, pp. 384-386, 2008.
Slivka et al., "Peptide Probes for Protein Transmembrane Domains" ACS Chem. Biol. 3(7):402-411, 2008.
http://www.lsbm.org/staff/hamakubo.html, Jul. 30, 2013 (13 pages).
Almen et al., "Mapping the Human Membrane Proteome: A Majority of the Human Membrane Proteins can be classified According to Function and Evolutionary Origin" BMC Biology 7:50, 2009 (14 pages).
http://www.nedo.go.jp/activities/portal/gaiyou/p06009/p06009.html, Dec. 2005 (1 page).
https://ruo.mbl.co.jp/custom/custom#sev.html, copyright 2008, Medical Biological Laboratories (2 pages).
Tam, "Synthetic Peptide Vaccin Design: Synthesis and Properties of a High-Density Multiple Antigenic Peptide System" Proc. Natl. Acad. Sci. USA 85:5409-5413, 1988.
Beck et al., "Nucleotide Sequence of the Gene ompA Coding the Outer Membrane Protein 11* of *Escherichia coli* K-12" Nucleic Acids Research 8(13):3011-3027, 1980.
Miraglia et al., "A Novel Five-Transmembrane Hematopoietic Stem Cell Antigen: Isolation, Characterization, and Molecular Cloning" Blood 90(12):5013-5021, 1997.
International Search Report for PCT/JP2012/050136, mailed Feb. 28,2012.
International Preliminary Report on Patentability for PCT/JP2012/050136, mailed Jul. 18, 2013.
Jul. 22, 2015 Office Action issued in U.S. Appl. No. 14/397,920.
Oct. 27, 2015 Office Action issued in U.S. Appl. No. 14/397,920.
Nov. 12, 2015 Office Action issued in U.S. Appl. No. 13/978,419.
Apr. 23, 2015 Office Action issued in U.S. Appl. No. 13/978,584.
Sep. 3, 2015 Office Action issued in U.S. Appl. No. 13/978,584.
Aug. 14, 2015 Office Action issued in U.S. Appl. No. 13/978,419.
Emmott et al., "Nucleolar targeting: the hub of the matter," EMBO reports, 2009, vol. 10, No. 3, pp. 231-238.
Goyal et al., "Phosphorylation-dependent Regulation of Unique Nuclear and Nucleolar Localization Signals of LIM Kinase 2 in Endothelial Cells," Journal of Biological Chemistry, 2006, vol. 281, No. 35, pp. 25223-25230.
Jul. 19, 2011 International Search Report issued in International Patent Application No. PCT/JP2011/062809.
Jan. 8, 2013 International Preliminary Report on Patentability issued in International Patent Application No.PCT/JP2011/062809.
Berendsen, "A Glimpse of the Holy Grail?," Science, vol. 282, No. 5389, pp. 642-643, Oct. 23, 1998.
Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.
Boursnell et al., "Sequences of the Nucleocapsid Genes from Two Strains of Avian Infectious Bronchitis Virus," J. Gen. Virol., vol. 66, pp. 573-580, 1985.
Bradley et al., "Limits of Cooperativity in a Structurally Modular Protein: Response of the Notch Ankyrin Domain to Analogous Alanine Substitutions in Each Repeat," J Mol. Biol, vol. 324, pp. 373-386, 2002.
Cserpén et al., "The Mechanism of Nuclear Transport of Natural or Artificial Transport Substrates in Digitonin-Permeabilized Cells," Journal of Cell Science, vol. 108, pp. 1849-1861, 1995.
Eiges et al., "Establishment of Human Embryonic Stem Cell-Transfected Clones Carrying a Marker for Undifferentiated Cells," Current Biology, vol. 11, pp. 514-518, 2001.
Fang et al., "Selection of and Recombination between Minor Variants Lead to the Adaptation of an Avian Coronavirus to Primate Cells," Biochemical and Biophysical Research Communications, vol. 336, pp. 417-423, 2005.
Futaki et al., "Intracellular Protein Delivery Using Membrane-Permeable Peptides," Seibutsu to Kagaku, vol. 43, No. 10, pp. 649-653, 2005.
Hilton et al., "Twenty Proteins Containg a C-Terminal SOCS Box Form Five Structural Classes," Proc. Natl. Acad. Sci. USA, vol. 95, pp. 114-119, Jan. 1998.
Kamura et al., "The Elongin BC Complex Interacts with the Conserved SOCS-Box Motif Present in Members of the SOCS, Ras, WD-40 Repeat, and Ankyrin Repeat Families," Genes & Development, vol. 12, pp. 3872-3881, 1998.
Kamura et al., "VHL-Box and SOCS-Box Domains Determine Binding Specificity for Cul2-Rbx1 and Cul5-Rbx2 Modules of Ubiquitin Ligases," Genes & Development, vol. 18, pp. 3055-3065, 2004.
Kang et al., "The Precursor of Alzheimer's Disease Amyloid A4 Protein Resembles a Cell-Surface Receptor," Nature, vol. 325, pp. 733-736, Feb. 19, 1987.
Kile et al., "The Suppressors of Cytokine Signalling (SOCS)," Cellular and Molecular Life Sciences, vol. 58, pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Liu et al., "Rack1 Competes with FISP90 for Binding to HIF-1? and is Required for O2-Independent and HSP90 Inhibitor-Induced Degradation of HIF-1?," Molecular Cell, vol. 25, pp. 207-217, Jan. 26, 2007.
Liu et al., "Calcineurin Promotes Hypoxia-Inducible Factor 1? Expression by Dephosphorylating RACK1 and Blocking Rack1 Dimerization," Journal of Biological Chemistry, vol. 282, No. 51, pp. 37064-37073, Dec. 21, 2007.
Liu et al., "Rack1 vs. HSP90: Competition for HIF-1? Degradation vs. Stablization," Cell Cycle, vol. 6, No. 6, pp. 356-659, Mar. 15, 2007.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.

(56) References Cited

OTHER PUBLICATIONS

NCBI database Accession No. Q1M2X0, p. 1, accessed Nov. 7, 2012.
Ngo et al., "Computational Complexity, Protein Structure Prediction, and the Levinthal Paradox," The Protein Folding Problem and Tertiary Structure Prediction, K. Merz Jr. and S. Le Grand, Eds. pp. 491-494, Birchhuser Bosino 1994.
Pokorska et al., "The Analysis of the Transcriptional Activator PrnA Reveals a Tripartite Nuclear Localisation Sequence," J. Mil. Biol., vol. 298, pp. 585-596, 2000.
Reed et al., "Delineation and Modelling of a Nucleolar Retention Signal in the Coronavirus Nucleocapsid Protein," Traffic, vol. 7, pp. 833-848, 2006.
Rudinger, "Peptide Hormones," JA Parsons, Ed., pp. 1-7, Jun. 1976.
"Designing Custom Peptides," www.sigma-genosys.com/peptide_design.asp <http://www.sigma-genosys.com/ peptide_design.asp>; Sigma-Genosys, pp. 1-2, accessed Dec. 16, 2004.
Sugaya et al., "Practical Issues in Stem Cell Therapy for Alzheimer's Disease," Curr. Alzheimer Res., vol. 4, No. 4, pp. 370-377, 2007.
Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Voet et al., "Biochemistry," John Wiley & Sons, Inc., pp. 235-241, 1995.
Yu et al., "Selective Assembly of HIV-1 Vif-Cul5-ElonginB-ElonginC E3 Ubiquitin Ligase Complex through a Novel SOCS Box and Upstream Cysteines," Genes & Development, vol. 18, pp. 2867-2872, 2004.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510.
Oct. 5, 2010 International Search Report issued in International Patent Application No. PCT/JP2010/062691.
Oct. 5, 2010 International Search Report issued in International Patent Application No. PCT/JP2010/062693.
Jan. 18, 2011 International Search Report issued in International Patent Application No. PCT/JP2010/069165.
Jun. 12, 2012 International Preliminary Report on Patentability and Written Opinion issued in International Patent Application No. PCT/JP2010/069165.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,539.
Nov. 14, 2012 Office Action issued in U.S. Appl. No. 13/386,582.
Jan. 31, 2013 Office Action issued in U.S. Appl. No. 13/258,788.
Feb. 22, 2013 Office Action issued in U.S. Appl. No. 13/386,539.
Feb. 22, 2013 Office Action issued in U.S. Appl. No. 13/386,582.
Apr. 17, 2013 Office Action issued in U.S. Appl. No. 13/503,220.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.
Dieterlen-Lievre, "On the Origin of Haemopoietic Stem Cells in the Avian Embryo: An Experimental Approach," J. Embryol. exp. Morph., vol. 33, No. 3, pp. 607-619, 1975.
Aug. 7, 2013 Office Action issued in U.S. Appl. No. 13/258,788.
Aug. 6, 2013 Office Action issued in U.S. Appl. No. 13/386,582.
Copani et al., "Mitotic Signaling by ?-amyloid Causes Neuronal Death," The FASEB Journal, vol. 13, pp. 2225-2234, Dec. 1999.
De Strooper et al., "Proteolytic Processing and Cell Biological Functions of the Amyloid Precursor Protein," Journal of Cell Science, vol. 113, pp. 1857-1870, 2000.
Zhang et al., "NSA2, A Novel Nucleolus Protein Regulates Cell Proliferation and Cell Cycle," Biochemical and Biophysical Research Communications, vol. 391, pp. 651-658, 2010.
Mar. 24, 2014 Office Action issued in European Application No. 10 826 811.1.
Apr. 22, 2014 Supplementary European Search Report issued in European Application No. 11 78 99252.
Neer et al., "The Ancient Regulatory-Protein Family of WD-Repeat Proteins," Nature, vol. 371, pp. 297-300, 1994.
Apr. 15, 2014 European Search Report issued in European Application No. 14153135.0.
Selkoe, "Normal and Abnormal Biology of the Beta-Amyloid Precursor Protein," Annu. Rev. Neurosci., vol. 17, pp. 489-517, 1994.
Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.
Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.
Kwak, "Studies on the Novel Function of Amyloid Precursor Protein in Glial Differentiation of Neural Stem Cells," Dissertation, pp. 1-173, 2006.

* cited by examiner

```
                              SEQUENCE LISTING

<160> NUMBER OF SEQ ID NOS: 4

<210> SEQ ID NO 1
<211> LENGTH: 17
<212> TYPE: PRT
<213> ORGANISM: Homo sapiens

<400> SEQUENCE: 1

Met Leu Pro Gly Leu Ala Leu Leu Leu Leu Ala Ala Trp Thr Ala Arg
1               5                   10                  15

Ala

<210> SEQ ID NO 2
<211> LENGTH: 17
<212> TYPE: PRT
<213> ORGANISM: Mus musculus

<400> SEQUENCE: 2

Met Leu Pro Ser Leu Ala Leu Leu Leu Leu Ala Ala Trp Thr Val Arg
1               5                   10                  15

Ala

<210> SEQ ID NO 3
<211> LENGTH: 17
<212> TYPE: PRT
<213> ORGANISM: Sus scrofa

<400> SEQUENCE: 3

Met Leu Pro Gly Leu Ala Leu Val Leu Leu Ala Ala Trp Thr Ala Arg
1               5                   10                  15

Ala

<210> SEQ ID NO 4
<211> LENGTH: 17
<212> TYPE: PRT
<213> ORGANISM: Cavia porcellus

<400> SEQUENCE: 4

Met Leu Pro Ser Leu Ala Leu Leu Leu Leu Thr Thr Trp Thr Ala Arg
1               5                   10                  15

Ala
```

SYNTHETIC PEPTIDE FOR INHIBITING EXPRESSION OF TYPE 2 TNF RECEPTOR AND USE THEREOF

TECHNICAL FIELD

The present invention relates to a synthetic peptide capable of selectively inhibiting the expression of type 2 TNF receptor in target cells. In particular, it relates to a type 2 TNF receptor expression-inhibiting composition comprising the peptide as an active ingredient and a method for inhibiting the expression of type 2 TNF receptor, using the peptide (the composition).

The present application claims priority based on Japanese Patent Application No. 2012-231148 filed on Oct. 18, 2012, and its entire contents are incorporated herein by reference.

BACKGROUND ART

Tumor necrosis factors generally called TNF (typically three types, namely TNF-α, TNF-β (LT-α), LT-β) are cytokines that are produced primarily in immune system cells. TNF-α being representative thereof is produced mainly in macrophages and shows various physiological activities such as small thrombi formation and apoptosis induction, etc. Excessive production (expression) of TNF-α is known to bring on diseases such as rheumatoid arthritis and the like.

As for the receptors to which such TNF binds, there are a type 1 TNF receptor (tumor necrosis factor receptor 1 or "TNF-R1" hereinafter) having a molecular weight of about 55 kDa and a type 2 TNF receptor (tumor necrosis factor receptor 2 or "TNF-R2" hereinafter) having a molecular weight of about 75 kDa.

These two types of TNF receptor are known to give rise to different, individual physiological effects. It is reported, for instance, that in a test with TNF-R1 knockout mice and TNF-R2 knockout mice, arteriogenesis of the upper limb and angiogenesis of the lower limb are enhanced in TNF-R1 knockout mice, but are impaired in TNF-R2 knockout mice (Non-Patent Document 1).

In the meantime, while glaucoma is the top cause for the loss of eyesight in our country and is becoming a serious problem in the aging society, it has been reported that the progress of glaucoma is slower in TNF-R2 knockout mice than in wild-type mice (oral presentation by S. McKinnon et al., "Neuroinflammation in Glaucoma" at XIX Biennial Meeting of the International Society for EYE RESEARCH, Jul. 18-23, 2010).

It is also reported that photoreceptor degeneration induced by retinal detachment is mediated by TNF-α acting via TNF-R2, but not much affected by TNF-R1 deficiency (Non-Patent Document 2).

CITATION LIST

Non-Patent Literature

[Non-Patent Document 1] American Journal of Pathology, vol. 169(5), 2006, pp. 1886-1898
[Non-Patent Document 2] Investigative Ophthalmology & Visual Science, vol. 52(3), 2011, pp. 1384-1391

SUMMARY OF INVENTION

As described above, while both being TNF receptors, TNF-R1 and TNF-R2 individually induce different physiological activities. In other words, it suggests that a TNF (e.g. TNF-α) mediates different physiological effects when the TNF binds to TNF-R1 and when it binds to TNF-R2.

This suggests that, for instance, if the expression of TNF-R2 can be reduced in a target organ, tissue or site (or more microscopically, in cells present in the organ, tissue or site) to modify (decrease) the relative presence of TNF-R2 compared to TNF-R1, it will be possible to disable (or inhibit) the manifestation of an undesirable physiological effect that would occur due to excessive expression of TNF-R2 in the organ, tissue or site.

For instance, as in the reported examples, with respect to retinal diseases such as glaucoma, retinal detachment, etc., by means of adjusting the proportions of the presence (expression) of TNF receptors present in retinal photoreceptor cells or ganglion cells to a lower relative presence (expression) of TNF-R2 than usual, apoptosis of the photoreceptor cells or ganglion cells can be inhibited.

However, there has hitherto been no method or drug for inhibiting TNF-R2 expression in TNF-R2-expressing cells thereby to reduce the relative presence of TNF-R2 compared to TNF-R1 present in the cell membrane, easily and highly efficiently.

The present invention has been thus made to provide a method for inhibiting the expression of TNF-R2 in at least one species of cells present in a desired organ, tissue or site, in vivo or in vitro, a synthetic peptide used in the method, and a composition (drug composition) comprising the peptide.

To achieve the objectives, the present invention provides a composition described below. In particular, the composition disclosed herein is for inhibiting the expression of TNF-R2 in cells capable of expressing type 2 TNF receptor (TNF-R2). The composition comprises a synthetic peptide essentially consisting of an amino acid sequence constituting an amyloid precursor protein (APP) signal peptide (or abbreviated to "APP signal sequence" hereinafter) or an amino acid sequence formed by substituting, deleting and/or adding one or several amino acid residues in/from/to the amino acid sequence of the signal peptide (or abbreviated to "modified APP signal sequence" hereinafter), and further comprises a pharmaceutically acceptable carrier.

Herein, the term "cells capable of expressing TNF-R2" refers to cells in which constant or temporary expression of TNF-R2 is observed in vivo or in vitro. For example, immune system cells and nervous system cells of humans and other mammals are typical examples of the cells referred to herein as being capable of expressing TNF-R2, that is, an approximately 75 kDa TNF receptor which includes no death domain and thus is clearly distinct from TNF-R1.

The present inventors closely studied the characteristics of amyloid precursor protein which is perceived as the causative substance of Alzheimer's disease in the amyloid hypothesis of Alzheimer's disease and took notice of the signal peptide of amyloid precursor peptide. The hypothesis suggests that amyloid precursor protein (APP) is cleaved by a secretase in neurons of the brain to produce an amyloid βprotein typically formed of 40 or 42 amino acid residues, and aggregation (accumulation) of the amyloid β in the brain destroys neurons, resulting in the onset of Alzheimer's disease.

The present inventors have come to complete this invention upon their discovery that when various TNF-R2-expressing cells (cultured cells) are supplied with a synthetic peptide consisting of an APP signal sequence or a modified APP signal sequence, the expression of TNF-R2 can be inhibited.

In other words, by supplying, to certain target cells capable of expressing TNF-R2, the "TNF-R2 expression-inhibiting peptide" which is the primary ingredient of the composition disclosed herein, or more specifically a synthetic peptide essentially consisting of an amino acid sequence constituting an amyloid precursor protein (APP) signal peptide or an amino acid sequence formed by substituting, deleting and/or adding one or several (typically two or three) amino acid residues in/from/to the amino acid sequence of the signal peptide (e.g. by supplying the composition or peptide according to the present invention to a culture medium in which the certain target cells capable of expressing TNF-R2 are being cultured), the expression of TNF-R2 can be inhibited in the cells supplied with the synthetic peptide.

By the use of the TNF-R2 expression-inhibiting composition (TNF-R2 expression-inhibiting peptide) disclosed herein, the TNF-R2 expression (i.e. its presence) in the target cells can be reduced. Thus, the TNF-R2 expression-inhibiting composition (TNF-R2 expression-inhibiting peptide) disclosed herein can contribute to treat or improve various TNF-mediated diseases and lesions, which are influenced by the expression (presence) of TNF-R2 or by the relative presence of TNF-R2 compared to TNF-R1. For instance, by reducing the expression (presence) of TNF-R2 in retinal photoreceptor cells or ganglion cells, apoptosis of the cells can be inhibited.

The TNF-R2 expression-inhibiting composition (TNF-R2 expression-inhibiting peptide) disclosed herein can be preferably used in research and development in fields (e.g. fields related to medicine, pharmacology, genetics, biochemistry, biology; the same applies hereinafter) aimed to improve diseases (disorders) mediated by TNF-R2.

The present invention also provides a method for inhibiting the expression of TNF-R2, the method characterized by the use of a synthetic peptide (TNF-R2 expression-inhibiting peptide) disclosed herein.

In other words, a method is provided for inhibiting the expression of TNF-R2 in cells capable of expressing TNF-R2, the method characterized by supplying the cells with a synthetic peptide essentially consisting of an amino acid sequence constituting an amyloid precursor protein (APP) signal peptide or an amino acid sequence formed by substituting, deleting and/or adding one or several amino acid residues in/from/to the amino acid sequence of the signal peptide According to such a method, in vivo or in vitro, the presence (expression) of TNF-R2 can be reduced in at least one species of cells that are present in a prescribed organ, tissue or site and are capable of expressing TNF-R2.

Thus, according to the present invention, by using a TNF-R2 expression-inhibiting composition (i.e. TNF-R2 expression-inhibiting peptide) disclosed herein, cells having a reduced presence of TNF-R2 can be produced. In other words, the present invention provides a method for producing cells having a reduced presence of TNF-R2, the method characterized by the use of the TNF-R2 expression-inhibiting composition (TNF-R2 expression-inhibiting peptide) disclosed herein.

In implementing the present invention, the amino acid sequence of the amyloid precursor protein (APP) signal peptide is preferably one of the following:

MLPGLALLLLAAWTARA (SEQ ID NO: 1)

MLPSLALLLLAAWTVRA (SEQ ID NO: 2)

MLPGLALVLLAAWTARA (SEQ ID NO: 3)

MLPSLALLLLTTWTARA (SEQ ID NO: 4)

By using the signal peptide of human (SEQ ID NO: 1), mouse (SEQ ID NO: 2), pig (SEQ ID NO: 3), guinea pig (SEQ ID NO: 4) origin or a modified APP signal sequence thereof, the expression of TNF-R2 can be inhibited in the target cells. The synthetic peptide used in practicing the present invention is preferably a chemically synthesized peptide having a total of 25 or fewer amino acid residues.

DESCRIPTION OF EMBODIMENTS

Preferred embodiments of the present invention are described below. Note that technical matters other than the matters particularly mentioned in the present description (e.g. the primary structure and chain length of a TNF-R2 expression-inhibiting peptide disclosed herein) which are required for carrying out the present invention (e.g., general matters relating to chemical peptide synthesis, cell cultivation, and preparation of a pharmaceutical composition containing a peptide) are matters of design variation that could be apprehended by a person skilled in the art based on conventional art in such fields as cell engineering, physiology, medicine, pharmacology, organic chemistry, biochemistry, genetic engineering, protein engineering, molecular biology, genetics, and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The present description incorporates by reference the entire contents of all the documents cited herein.

In the present description, the term "synthetic peptide" refers to a peptide fragment that is manufactured by artificial chemical synthesis or biosynthesis (i.e. genetic engineering-based production) and can stably exist in a certain composition (e.g., a TNF-R2 expression-inhibiting composition).

In this description, the term "peptide" refers to an amino acid polymer having a plurality of peptide bonds, and is not limited by the number of amino acid residues included in the peptide chain, with the term typically referring to one having a relatively small molecular weight with a total of 50 or fewer (e.g. 25 or fewer, especially 20 or fewer) amino acid residues.

In this description, unless otherwise specified, the term "amino acid residue" includes the N-terminal amino acid and the C-terminal amino acid of a peptide chain.

In this description, the term "modified APP signal sequence" refers to an amino acid sequence formed by substituting, deleting and/or adding (inserting) one or several (e.g. two or three) amino acid residues in a selected APP signal sequence without impairing its function (i.e. the ability to inhibit the expression of TNF-R2). Typical examples of the modified APP signal sequence referred to in the present description include a sequence generated by conservative amino acid replacement in an APP signal sequence disclosed herein, where one or several (typically two or three) amino acid residues are conservatively substituted (e.g. a hydrophobic amino acid residue is substituted with a different hydrophobic amino acid residue, e.g. mutual substitution between a leucine residue and a valine residue; a neutral amino acid residue is substituted with a different neutral amino acid residue, e.g. mutual substitution between a glycine residue and a serine residue), an amino acid sequence corresponding to a selected amino acid sequence with addition (insertion) or deletion of one or several (typically two or three) amino acid residues, and the like.

In this description, the term "polynucleotide" refers to a polymer (nucleic acids) in which several nucleotides are linked by phosphodiester bonds, but not limited by the number of nucleotides. As used herein, the term 'polynucleotide' encompasses DNA fragments and RNA fragments of various lengths.

The composition used in the method disclosed herein for inhibiting TNF-R2 expression comprises the TNF-R2 expression-inhibiting peptide as an active ingredient.

As described above, the TNF-R2 expression-inhibiting peptide disclosed herein can be perceived as a synthetic peptide that does not exist in nature in view that it is a synthetic peptide essentially consisting of an APP signal sequence or a modified APP signal sequence thereof.

Table 1 shows preferable examples of an APP signal sequence constituting the TNF-R2 expression-inhibiting peptide disclosed herein.

TABLE 1

| No. | Amino acid sequence | Number of total amino acid residues |
|---|---|---|
| 1 | MLPGLALLLLAAWTARA (SEQ ID NO: 1) | 17 |
| 2 | MLPSLALLLLAAWTVRA (SEQ ID NO: 2) | 17 |
| 3 | MLPGLALVLLAAWTARA (SEQ ID NO: 3) | 17 |
| 4 | MLPSLALLLLTTWTARA (SEQ ID NO: 4) | 17 |

Among these listed amino acid sequences, the amino acid sequence of SEQ ID NO: 1 is a human APP signal sequence. The amino acid sequence of SEQ ID NO: 2 is a mouse APP signal sequence. The amino acid sequence of SEQ ID NO: 3 is a pig APP signal sequence. The amino acid sequence of SEQ ID NO: 4 is a guinea pig APP signal sequence.

In the TNF-R2 expression-inhibiting peptide disclosed herein, at least one amino acid residue is preferably amidated. Amidation of a carboxyl group in an amino acid residue (typically the C-terminal amino acid residue of the peptide chain) may increase the structural stability (e.g., protease resistance) of the synthetic peptide.

In the synthetic peptide used, the total number of amino acid residues constituting the peptide chain is suitably 50 or fewer, desirably 30 or fewer, for instance, 25 or fewer (e.g. 20 or fewer, typically 17 or 18 to 20). The number of amino acid residues in an APP signal sequence is within such a range. A peptide consisting of an APP signal sequence or a modified APP signal sequence is preferably used in the method disclosed herein.

The TNF-R2 expression-inhibiting peptide disclosed herein should just comprise, as an essential constituent (primary constituent), an APP signal sequence or a modified APP signal sequence. As long as the physiological activity of interest is not lost, the peptide may comprise other amino acid residue(s) besides the APP signal sequence or the modified APP signal sequence.

Such a short chain peptide can be easily prepared by chemical synthesis. Thus, the TNF-R2 expression-inhibiting peptide can be readily provided. Although no particular limitation is imposed on the conformation (spatial structure) of the peptide as long as the activity of interest is exhibited in the environment employed (in vitro or in vivo), a linear or a helical conformation is preferable from the standpoint of the less likelihood of becoming an immunogen (antigen), a preferable peptide has. A peptide having such a conformation is preferable also from the standpoint of the low susceptibility to epitope formation.

It is noted that in the TNF-R2 expression-inhibiting peptide disclosed herein, while all amino acid residues are preferably L-amino acids, some or all of the amino acid residues may be substituted with D-amino acids.

The synthetic peptide disclosed herein can be easily manufactured according to conventional chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group. For the synthetic peptide disclosed herein, a peptide chain having a desired amino acid sequence and a portion with modification (e.g., C-terminal amidation) can be synthesized by solid-phase synthesis using a commercial peptide synthesizer (which is, for instance, available from PerSeptive Biosystems, Applied Biosystems, etc.).

Alternatively, the TNF-R2 expression-inhibiting peptide may be biosynthesized based on genetic engineering techniques. In particular, a polynucleotide (typically a DNA strand) is synthesized so as to have a nucleotide sequence (including the ATG initiation codon) encoding the amino acid sequence of the desired peptide. Then, in accordance with the host cells, a recombinant vector is constructed so as to have an expression gene construct composed of the synthesized polynucleotide (DNA) and various regulatory elements (including promoters, ribosome binding sites, terminators, enhancers, and various cis-elements which control the expression level) to allow expression of the amino acid sequence within the host cells.

By an ordinary technique, this recombinant vector is inserted into prescribed host cells, and the host cells, or tissue or a mass containing these cells are cultured under specific conditions. In this way, the target TNF-R2 expression-inhibiting peptide can be expressed and produced intracellularly.

The target TNF-R2 expression-inhibiting peptide can be obtained by isolating the peptides from the host cells (from the culture medium if secreted) and purifying it. Methods hitherto used in the art may be directly employed without modification for constructing the recombinant vector and introducing the constructed recombinant vector into the host cell. Because such methods themselves are not distinctive to the present invention, detailed description is omitted.

For example, a fusion protein expression system may be employed to allow efficient large-scale production in host cells. In particular, a gene (DNA) coding for the amino acid sequence of the target TNF-R2 expression-inhibiting peptide is chemically synthesized, and the synthesized gene is introduced to a preferred site on a fusion protein expression vector (e.g. GST (glutathione S-transferase) fusion protein expression vectors such as the pET series available from Novagen as well as the pGEX series available from Amersham Bioscience). Host cells (typically, *Escherichia coli*) are then transformed by the vector. The resulting transformant is cultured to produce the target fusion protein. This protein is then extracted and purified. Subsequently, the purified fusion protein is cleaved with a specific enzyme (protease), and the liberated target peptide fragments (the designed TNF-R2 expression-inhibiting peptide) are collected by a method such as affinity chromatography. The TNF-R2 expression-inhibiting peptide disclosed herein can be produced by using such a fusion protein expression system heretofore known (e.g., the GST/His system available from Amersham Bioscience may be used).

Alternatively, the target peptide may be synthesized in vitro by constructing a template DNA for a cell-free protein synthesis system (i.e. a synthesized gene fragment having a nucleotide sequence that codes for the amino acid sequence of the TNF-R2 expression-inhibiting peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., Nature Biotechnology, 19, 751-755 (2001), and Madin et al., Proc. Natl. Acad. Sci. USA, 97(2), 559-564 (2000). Based on the technology described in these articles, many corporations have been conducting contract manufacturing of peptides at the time when this application was filed. Also, wheat germ cell-free protein synthesis kits (such as PROTEIOS™ available from Toyobo Co., Ltd. of Japan) are commercially available.

By a heretofore known method, can be easily produced (synthesized) a single-stranded or double-stranded polynucleotide containing a nucleotide sequence encoding the TNF-R2 expression-inhibiting peptide disclosed herein and/ or a nucleotide sequence complementary thereto. In other words, by selecting a codon corresponding to the respective amino acid residues constituting the designed amino acid sequence, a nucleotide sequence corresponding to the amino acid sequence of the TNF-R2 expression-inhibiting peptide can be easily determined and provided. Once the nucleotide sequence is determined, by utilizing a DNA synthesizer, etc., can be easily obtained a polynucleotide (single strand) corresponding to the desired nucleotide sequence. Furthermore, the target double-stranded DNA can be obtained by using the resulting single-stranded DNA as a template and employing various enzymatic synthetic methods (typically PCR).

The polynucleotide provided by the present invention may be in the form of DNA or RNA (mRNA, etc.). The DNA can be provided as a double strand or a single strand. When it is provided as a single strand, it may be a coding strand (sense strand) or an anticoding strand (anti-sense strand) complementary thereto.

The polynucleotide provided by the present invention can be used as a material for constructing a recombinant DNA (expression cassette) for producing the TNF-R2 expression-inhibiting peptide in various host cells or in a cell-free protein synthesis system.

The TNF-R2 expression-inhibiting peptide disclosed herein can inhibit the expression of TNF-R2, by acting on target cells capable of expressing TNF-R2, such as central or peripheral nervous system cells, immune system cells, vascular cells and other cardiovascular system cells, retinal cells and other ocular cells and the like. Thus, it can be preferably used as an active ingredient in a composition (i.e. pharmaceutical composition) for decreasing the expression (presence) of TNF-R2, in other words, as a composition (pharmaceutical composition) for reducing the relative presence of TNF-R2 compared to TNF-R1.

Such a TNF-R2 expression-inhibiting peptide may be in a salt form as far as the physiological activity is not impaired. For example, it is possible to use an acid salt of the peptide, which can be obtained by adding a commonly used inorganic or organic acid in accordance with an ordinary technique. Alternatively, it can be a different type of salt (e.g. a metal salt). The "synthetic peptide" in this description and in claims encompasses such salts.

The composition disclosed herein may contain various pharmaceutically (medically) acceptable carriers in accordance with the application form, as far as the TNF-R2 expression-inhibiting peptide as the active ingredient is maintained physiologically active. Carriers generally used as diluents or excipients in peptide medications are preferred. Although it may suitably vary depending on the intended purpose and application, typical examples include water, physiological buffers and various organic solvents. The carrier may be an aqueous alcohol (ethanol or the like) solution at an appropriate concentration, glycerol, or non-drying oil such as olive oil. Alternatively, it may be a liposome. Examples of secondary ingredients that may be contained in such a composition include various fillers, bulking agents, binders, wetting agents, surfactants, dyes, fragrances and the like.

Typical examples of the form of the composition disclosed herein include liquid formulas, suspensions, emulsions, aerosols, foams, granules, powders, tablets, capsules, ointments, aqueous gels and the like. For injection, etc., it may be formulated as a freeze-dried product or pellets to prepare a drug solution by dissolving it in saline or a suitable buffer (e.g., PBS) just prior to use.

The process itself of preparing a composition (drug) in various forms with the TNF-R2 expression-inhibiting peptide (primary ingredient) and various carriers (secondary ingredients) may be carried out in accordance with a heretofore known method. Because such a preparation process itself is not distinctive to the present invention, detailed description is omitted. The detail information regarding formulations can be found in, for example, Comprehensive Medicinal Chemistry, edited by Corwin Hansch and published by Pergamon Press (1990). The entire contents of this book are incorporated in this description by reference.

The target organ, tissue or site to which the present invention is applied is not particularly limited as long as there are cells capable of expressing TNF-R2 in the target. Preferable examples include cells (e.g. neurons, glial cells) of the central nervous system such as the brain and spinal cord or of the peripheral nervous system, immune system cells (e.g. various lymphocytes, macrophages, neutrophils, eosinophils, basophils, monocytes). The present invention can be applied to cells of the cardiovascular system including blood vessels (e.g. cardiac myocytes constituting the heart, vascular endothelial cells), retinal cells, and so on.

Alternatively, the present invention can be applied to carcinoma cells (tumor cells) in various cancers (tumors).

Alternatively, the present invention can be applied to stem cells including ES cells (embryotic stem cells), iPS cells (induced pluripotent stem cells), adipose stem cells, mesenchymal stem cells such as cartilage stem cells, hematopoietic stem cells, neural stem cells, and so on.

The TNF-R2 expression-inhibiting peptide (or the composition comprising the peptide) disclosed herein can be used according to a method and dosage appropriate for the form and purpose.

For example, with respect to cells (a cell cluster), tissue or an organ under in vitro incubation, the peptide of interest can be supplied to a culture medium containing the target cultured cells (cultured tissue or organ). Its amount and the number of portions to be added are not particularly limited as they may vary in accordance with the conditions such as the type of cultured product, cell density (initial cell density at the incubation start), passage number, incubation conditions, type of culture medium, etc. When human or non-human mammalian cells, tissue and the like are cultured, it can be added in one to several portions so that the concentration of the peptide in the culture medium is within a range of about 0.1 µM to 100 µM or more preferably within a range of 0.5 µM to 20 µM (e.g., 1 µM to 10 µM).

By supplying the TNF-R2 expression-inhibiting peptide disclosed herein to an in vitro culture system, the expression of TNF-R2 can be inhibited in the culture system, whereby the relative presence of TNF-R2 compared to TNF-R1 can be reduced.

Examples of preferable mammals to which the present is applied include rodents such as mice, rats, guinea pigs, etc.; odd-toed ungulates such as horses, donkeys, etc.; even-toed ungulates such as pigs, cows, etc.; primates (excluding humans) such as chimpanzees, orangutans, crab-eating monkeys, etc.; and the like.

Alternatively, in order to inhibit TNF-R2 expression to reduce the relative presence of TNF-R2 compared to TNF-R1 in a prescribed organ, tissue or site (or a tissue fragment or cell cluster transplanted in a prescribed site) in vivo, a suitable amount of a TNF-R2 expression-inhibiting peptide can be prepared into a liquid formula and administered in a desirable amount to the patient (i.e. in vivo) by intravenous, intramuscular, subcutaneous, intradermal, or intraperitoneal injection.

Alternatively, it can be administered directly to the prescribed tissue (i.e., cells constituting the tissue) in a solid form such as tablets, etc., in a gel form such as ointment, etc., or in an aqueous gel form. The amount and the number of portions to be added are not particularly limited as they may vary depending on conditions such as the type of cells subjected to balance adjustment for their presence, the site, organ or tissue where the cells are present, etc.

Several worked examples related to the present invention are described below while these examples are not intended to limit the scope of the invention.

EXAMPLE 1

Peptide Synthesis

Using the peptide synthesizer described later, were prepared a synthetic peptide consisting of the amino acid sequence of SEQ ID NO: 1 shown in Table 1 above and a synthetic peptide consisting of the amino acid sequence of SEQ ID NO: 2. In the description below, the two synthetic peptides in total are referred to as Sample 1 and Sample 2 corresponding to their SEQ ID NOS. These are chemically synthesized linear peptides each formed of a total of 17 amino acid residues. Each peptide was synthesized by carrying out solid-phase synthesis (Fmoc chemistry), operating a commercial peptide synthesizer (an Intavis AG system) in accordance with the operation manual. Because the mode of using the peptide synthesizer itself is not distinctive to the present invention, detailed description is omitted. Each synthetic peptide was dissolved in DMSO and diluted with PBS (phosphate buffered saline) to prepare a 1 mM stock solution.

EXAMPLE 2

Test of Each Synthetic Peptide for TNF-R2 Expression-Inhibiting Activity with Cell Line of Mouse Origin The activities of the two peptides synthesized in Example 1 above were tested with cultured cells of a mouse spinal cord, neuroblastoma cell line (Neuro 2a). The control group was supplied with no peptides. The test details are described below.

The Neuro 2a cell line was seeded in a culture dish of 6 cm diameter at a density of $8.5 \times 10^4$ cells/mL and incubated overnight in a general DMEM culture medium (with 10% FBS, 1% penicillin) at 37° C. in a $CO_2$ incubator at 5% $CO_2$.

After incubated overnight, the culture medium was replaced with a DMEM culture medium containing 2% FBS, 20 µM retinoic acid and 1% penicillin. Incubation was carried on for seven days under the same conditions to effect retinoic acid induction. Subsequently, the culture medium was replaced with a DMEM culture medium containing the peptide of Sample 1 or Sample 2 in an amount equivalent to 5 µM, in addition to 2% FBS, 20 µM retinoic acid and 1% penicillin (also containing 12.5 µL of DMSO at this point). Incubation was carried on under the same conditions for two days. The control group (group supplied with no peptide) was incubated for two days in a DMEM culture medium (with 2% FBS, 20 µM retinoic acid, 1% penicillin) supplied only with the aforementioned amount of DMSO, without any peptide.

After completion of the incubation, cultured cells in each test group were collected and divided into certain test tubes in fractions having the same number of cells. By the immunofluorescence technique described below, the expression (presence) of TNF-R1 and TNF-R2 was then assessed in each test group (group supplied with no peptide, group supplied with Sample 1, group supplied with Sample 2).

More specifically, in each test group, for the TNF-R2 measurement, an anti-TNF-R2 goat polyclonal antibody (a Santa Cruz Biotechnology, Inc. product, SC-1074) was added to the respective test tubes to a final concentration of $4 \times 10^{-3}$ mg/mL and incubation was carried out at 37° C. for a prescribed time period. As a secondary antibody, a donkey anti-goat IgG antibody (an Invitrogen product, A11055) labeled with a fluorescent dye (Alexa® 488) was added to the test tubes to a final concentration of $4 \times 10^{-3}$ mg/mL and incubation was carried out at 37° C. for a prescribed time period.

On the other hand, as for the TNF-R1 measurement, an anti-TNF-R1 rabbit polyclonal antibody (a Santa Cruz Biotechnology, Inc. product, SC-7895) was added to the respective test tubes to a final concentration of $4 \times 10^{-3}$ mg/mL and incubation was carried out at 37° C. for a prescribed time period. As a secondary antibody, a goat anti-rabbit IgG antibody (an Invitrogen product, A11034) labeled with a fluorescent dye (Alexa® 488) was added to the test tubes to a final concentration of $2 \times 10^{-3}$ mg/mL and incubation was carried out at 37° C. for a prescribed time period.

Figure 1:
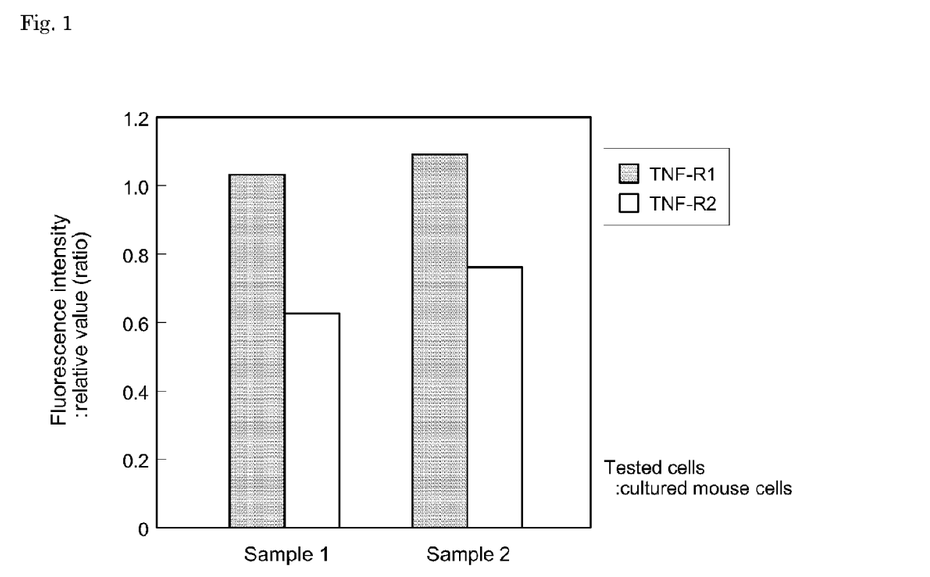
FIG. 1 shows a graph plotting the presence of TNF-R2 relative to the presence of TNF-R1 in cultured cells of mouse origin based on immunofluorescence assays using an anti-TNF-R1 polyclonal antibody and an anti-TNF-R2 polyclonal antibody (primary antibodies) along with a fluorescent dye-labeled secondary antibody.

The fluorescence intensities of cells were measured with a flow cytometer (a Millipore system product, Guava® easyCyte 8HT). The results are shown in FIG. 1. For both TNF-R2 and TNF-R1, the fluorescence intensities are shown as relative values with the fluorescence intensities of TNF-R2 and TNF-R1 in the control group (group supplied with no peptide) being 1, respectively.

As shown in FIG. 1, when either Sample 1 or Sample 2 was supplied to the cultured cells of mouse origin, the presence (expression) of TNF-R2 significantly decreased as compared with the control group. This indicates that each synthetic peptide synthesized as Sample 1 or Sample 2 is highly active as a TNF-R2 expression-inhibiting peptide.

On the other hand, irrespective of whether Sample 1 or Sample 2 was supplied to the cultured mouse cells, no significant change was observed in the presence (expression) of TNF-R1 as compared with the control group (the expression of TNF-R1 slightly increased as compared with the control group). Accordingly, by using a synthetic peptide essentially consisting of an APP signal sequence such as Sample 1 or Sample 2, the expression of TNF-R2 can be inhibited in a target organ, tissue or site (microscopically, in cells present in the organ, tissue or site), and also the relative presence of TNF-R2 can be decreased, compared to TNF-R1.

EXAMPLE 3

Test of Each Synthetic Peptide for TNF-R2 Expression-Inhibiting Activity with Cell Line of Human Origin The activities of the two peptides synthesized in Example 1 above were tested with cultured cells of a human neuroblastoma cell line (SK-N-SH). The control group was supplied with no peptides. The test details are described below.

The SK-N-SH cell line was seeded in a 4 mL fraction in a culture dish of 6 cm diameter at a density of $1.5 \times 10^5$ cells/mL and incubated in a general DMEM culture medium (with 10% FBS, 2 mM L-glutamine, 50 unit/mL penicillin, and 50 μg/mL streptomycin) at 37° C. in a $CO_2$ incubator at 5% $CO_2$ over two nights.

After incubated over two nights, the culture medium was replaced with a DMEM culture medium with 2% FBS, 2 mM L-glutamine, 20 μM retinoic acid, 50 unit/mL penicillin, and 50 μg/mL streptomycin. Incubation was carried on for five days under the same conditions to effect retinoic acid induction. Subsequently, the culture medium was replaced with a DMEM culture medium containing the peptide of Sample 1 or Sample 2 in an amount equivalent to 5 μM, in addition to 2% FBS, 2 mM L-glutamine, 20 μM retinoic acid, 50 unit/mL penicillin and 50 μg/mL streptomycin (also containing 5 μL of DMSO at this point). Incubation was carried on under the same conditions for two days. The control group (group supplied with no peptide) was incubated for two days in a DMEM culture medium (with 2% FBS, 2 mM L-glutamine, 20 μM retinoic acid, 50 unit/mL penicillin, and 50 μg/mL streptomycin) supplied only with the aforementioned amount of DMSO, without any added peptide.

After completion of the incubation, cultured cells in each test group were collected and divided into certain test tubes in fractions having the same number of number of cells. By the immunofluorescence technique described below, the expression (presence) of TNF-R1 and TNF-R2 was then assessed in each test group (group supplied with no peptide, group supplied with Sample 1, group supplied with Sample 2).

More specifically, in each test group, for the TNF-R2 measurement, the respective test tubes were supplemented with an anti-TNF-R2 goat polyclonal antibody (a Santa Cruz Biotechnology, Inc. product, SC-1074) to a final concentration of $4 \times 10^{-3}$ mg/mL and were left standing still on ice for a prescribed time period. As for a secondary antibody, the test tubes were supplemented with a donkey anti-goat IgG antibody (an Invitrogen product, A21447) labeled with a fluorescent dye (Alexa® 647) to a final concentration of $4 \times 10^{-3}$ mg/mL and were left standing still on ice for a prescribed time period.

On the other hand, as for the TNF-R1 measurement, the respective test tubes were supplemented with an anti-TNF-R1 mouse monoclonal antibody (a Santa Cruz Biotechnology, Inc. product, SC-52739) to a final concentration of $2 \times 10^{-3}$ mg/mL and were left standing still on ice for a prescribed time period. As for a secondary antibody, the test tubes were supplemented with a goat anti-mouse IgG antibody (an Invitrogen product, A10029) labeled with a fluorescent dye (Alexa® 488) at a final concentration of $4 \times 10^{-3}$ mg/mL and were left standing still on ice for a prescribed time period for incubation.

Figure 2:
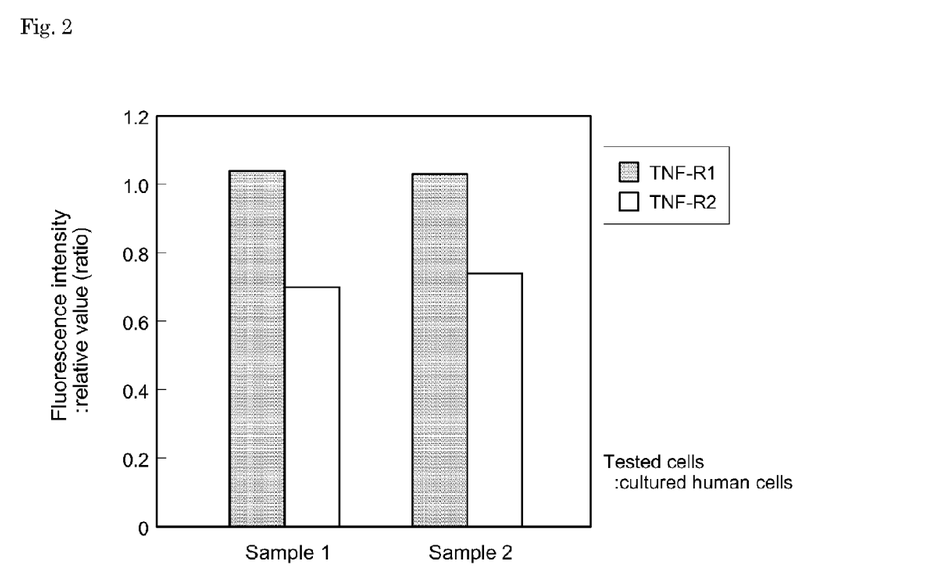
FIG. 2 shows a graph plotting the presence of TNF-R2 relative to the presence of TNF-R1 in cultured cells of human origin based on immunofluorescence assays using an anti-TNF-R1 polyclonal antibody and an anti-TNF-R2 polyclonal antibody (primary antibodies) along with a fluorescent dye-labeled secondary antibody.

The fluorescence intensities of cells were measured with a flow cytometer (a Millipore system product, Guava® easyCyte 8HT). The results are shown in FIG. 2. For both TNF-R2 and TNF-R1, the fluorescence intensities are shown as relative values with the fluorescence intensities of TNF-R2 and TNF-R1 in the control group (group supplied with no peptide) being 1, respectively.

As shown in FIG. 2, when either Sample 1 or Sample 2 was supplied to the cultured cells of human origin, the presence (expression) of TNF-R2 significantly decreased as compared with the control group. This indicates that each synthetic peptide synthesized as Sample 1 or Sample 2 is highly active as a TNF-R2 expression-inhibiting peptide.

On the other hand, irrespective of whether Sample 1 or Sample 2 was supplied to the cultured human cells, no significant change was observed in the presence (expression) of TNF-R1 as compared with the control group (the expression of TNF-R1 slightly increased as compared with the control group). Accordingly, by using a synthetic peptide essentially consisting of an APP signal sequence such as Sample 1 or Sample 2, the expression of TNF-R2 can be inhibited in a target organ, tissue or site (microscopically, in cells present in the organ, tissue or site), and also the relative presence of TNF-R2 can be decreased, compared to TNF-R1.

EXAMPLE 4

Preparation of Granular Formulation 50 mg of the synthetic peptide (a TNF-R2 expression-inhibiting peptide), 50 mg of a crystalline cellulose and 400 mg of lactose were mixed. The mixture was kneaded with 1 mL of an ethanol and water mixture. The kneaded mixture was granulated by a conventional method to obtain a granular formulation (granular composition) comprising the TNF-R2 expression-inhibiting peptide disclosed herein as the primary ingredient.

INDUSTRIAL APPLICABILITY

As described above, according to the present invention, the expression of TNF-R1 and TNF-R2 can be inhibited in cells present in a target organ, tissue or site. Accordingly, the present invention can contribute to treat or improve various TNF-mediated diseases and lesions, influenced by a relatively high expression (presence) of TNF-R2 or of a relatively high relative presence of TNF-R2 compared to TNF-R1. The present invention can be preferably implemented also in research and development in fields aimed to improve diseases (disorders) mediated by TNF-R2.

[Sequence Listing Free Text]
[Sequence Listing]
TG13-006 PCT ST25.txt

The invention claimed is:

1. A method for producing cells having a reduced relative presence of TNF-R2 compared to TNF-R1, the method comprising:
   culturing cells capable of expressing a TNF-R2 in a culture medium,
   supplying an artificially synthesized peptide essentially consisting of the amino acid sequence constituting an entire signal peptide of an amyloid precursor protein (APP) to the medium in which the cells are being cultured,
   further culturing the cells in the medium containing the artificially synthesized peptide to inhibit expression of TNF-R2 in the cells, and
   assessing expression of TNF-R2 in the cells.

2. The method according to claim 1, further comprising collecting the cells after the step of further culturing.

3. The method according to claim 1, wherein the amino acid sequence constituting the signal peptide of the amyloid precursor protein is:

MLPGLALLLLAAWTARA, (SEQ ID NO: 1)

MLPSLALLLLAAWTVRA, (SEQ ID NO: 2)

-continued

MLPGLALVLLAAWTARA, (SEQ ID NO: 3)

or

MLPSLALLLLTTWTARA. (SEQ ID NO: 4)

4. The method according to claim 1, wherein the amino acid sequence constituting the signal peptide of the amyloid precursor protein is

MLPGLALVLLAAWTARA, (SEQ ID NO: 3)

or

MLPSLALLLLTTWTARA. (SEQ ID NO: 4)

5. The method according to claim 1, wherein the cells are human or other mammalian nervous system cells.

6. The method according to claim 1, wherein the cells are human or other mammalian retinal cells or other ocular cells.

* * * * *